US011103711B2

(12) United States Patent
Shah et al.

(10) Patent No.: US 11,103,711 B2
(45) Date of Patent: Aug. 31, 2021

(54) SYSTEM AND METHOD FOR ENSURING A CONSISTENT CONNECTION OF ELECTRODES TO A REPLACEMENT IMPLANTABLE MEDICAL DEVICE

(71) Applicant: Boston Scientific Neuromodulation Corporation, Valencia, CA (US)

(72) Inventors: Chirag Shah, Valencia, CA (US); G. Karl Steinke, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 141 days.

(21) Appl. No.: 16/128,128

(22) Filed: Sep. 11, 2018

(65) Prior Publication Data

US 2019/0099606 A1  Apr. 4, 2019

Related U.S. Application Data

(60) Provisional application No. 62/568,111, filed on Oct. 4, 2017.

(51) Int. Cl.
*A61N 1/36* (2006.01)
*A61N 1/375* (2006.01)
(Continued)

(52) U.S. Cl.
CPC ......... *A61N 1/3752* (2013.01); *A61N 1/0534* (2013.01); *A61N 1/08* (2013.01);
(Continued)

(58) Field of Classification Search
CPC ....... A61N 1/08; A61N 1/0551; A61N 1/3787
See application file for complete search history.

(56) References Cited

U.S. PATENT DOCUMENTS 4,964,407 A  10/1990  Baker, Jr. et al.
6,181,969 B1  1/2001  Gord
(Continued)

FOREIGN PATENT DOCUMENTS

AU  2015218508 B2  8/2017

OTHER PUBLICATIONS

U.S. Appl. No. 62/557,640, Steinke et al., filed Sep. 12, 2017.
(Continued)

*Primary Examiner* — Michael J D Abreu
(74) *Attorney, Agent, or Firm* — Lewis & Reese, PLLC

(57) ABSTRACT

Implantable medical devices (IMD) such as those used in Deep Brain Stimulation application are commonly replaced when the device's useful life expires. At the time of replacement, the electrodes that were connected to the initial IMD are typically reused with the replacement IMD. It is desirable for the replacement IMD to utilize the stimulation parameters that were being utilized to provide stimulation in the initial IMD, but it is important that the electrodes be connected to the replacement IMD in a similar manner as they were connected to the initial IMD if stimulation parameters are reused. A connected electrode profile that includes measurements of electrical parameters associated with the electrodes can be generated in the initial IMD and the replacement IMD, and the profiles can be compared to determine whether the electrodes are connected in a similar manner in the replacement IMD as they were in the initial IMD.

16 Claims, 12 Drawing Sheets

(51) Int. Cl.
    *A61N 1/05*     (2006.01)
    *A61N 1/08*     (2006.01)

(52) U.S. Cl.
    CPC ....... *A61N 1/3603* (2017.08); *A61N 1/36125* (2013.01); *A61N 1/36171* (2013.01); *A61N 1/36192* (2013.01); *A61N 2001/083* (2013.01)

(56) References Cited

U.S. PATENT DOCUMENTS

| | | |
|---|---|---|
| 7,831,307 B1 | 11/2010 | Moffitt |
| 8,463,402 B2 | 6/2013 | Zhu et al. |
| 8,606,362 B2 | 12/2013 | He et al. |
| 8,620,436 B2 | 12/2013 | Parramon et al. |
| 8,731,679 B2 | 5/2014 | Ternes et al. |
| 8,761,897 B2 | 6/2014 | Kaula et al. |
| 8,768,453 B2 | 7/2014 | Parramon et al. |
| 9,061,140 B2 | 6/2015 | Shi et al. |
| 9,089,704 B2 | 7/2015 | Kelly |
| 9,302,100 B2 * | 4/2016 | Gunderson .......... A61N 1/3706 |
| 9,446,243 B2 | 9/2016 | Marnfeldt et al. |
| 9,724,508 B2 | 8/2017 | Lamont et al. |
| 2005/0033370 A1 * | 2/2005 | Jelen .................. A61N 1/36185 607/36 |
| 2007/0100407 A1 | 5/2007 | Armstrong |
| 2011/0054551 A1 | 3/2011 | Zhu et al. |
| 2011/0112609 A1 | 5/2011 | Peterson |
| 2012/0101545 A1 | 4/2012 | Wahlstrand et al. |
| 2012/0191153 A1 | 7/2012 | Swerdlow et al. |
| 2013/0184794 A1 | 7/2013 | Feldman et al. |
| 2013/0304139 A1 | 11/2013 | Musley et al. |

OTHER PUBLICATIONS

International Search Report and Written Opinion regarding corresponding PCT Application No. PCT/US2018/050502, dated Nov. 30, 2018.

\* cited by examiner

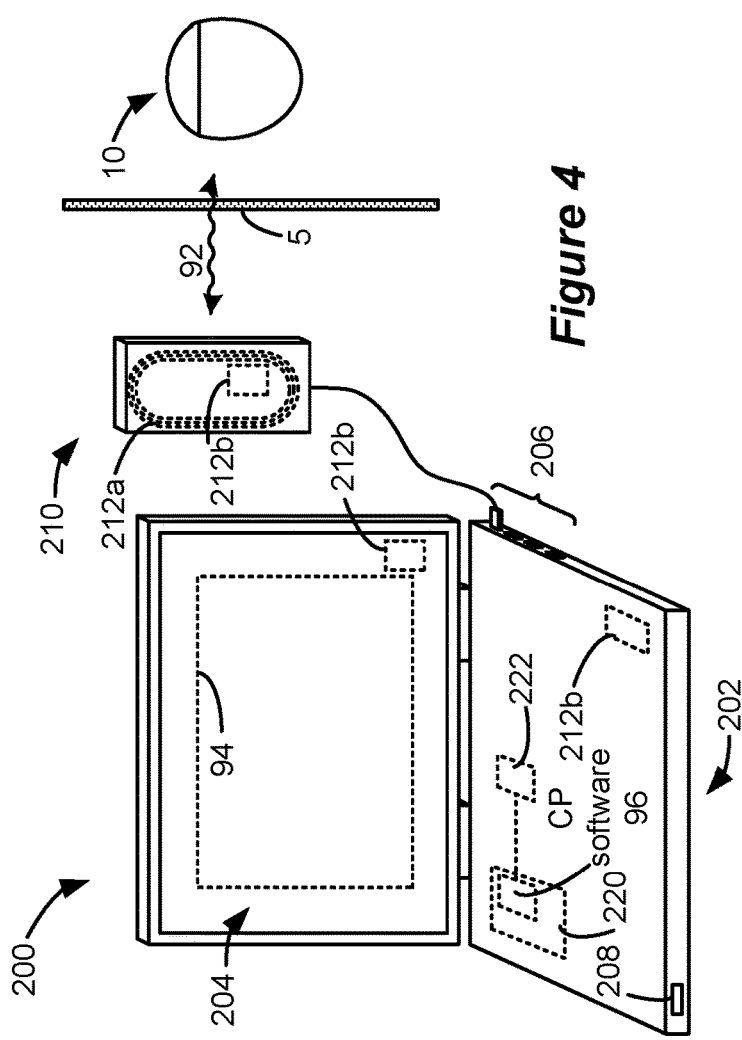
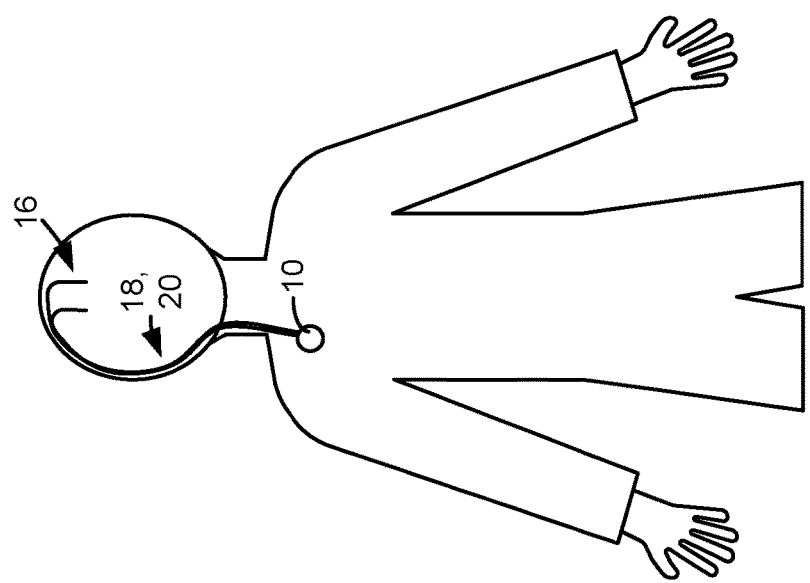
Figure 4
Figure 3

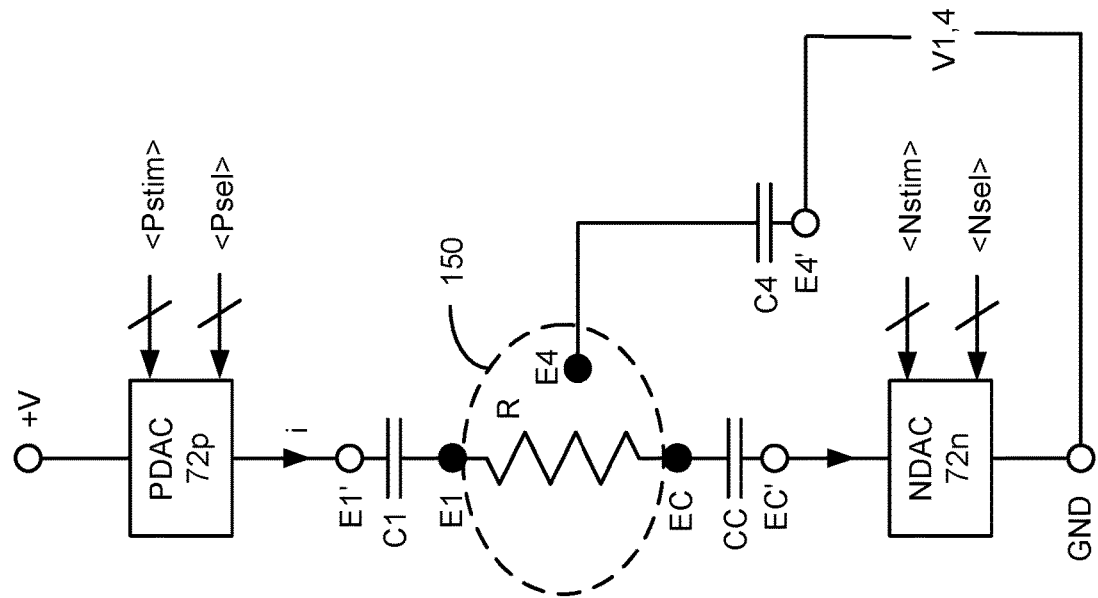
Figure 11C
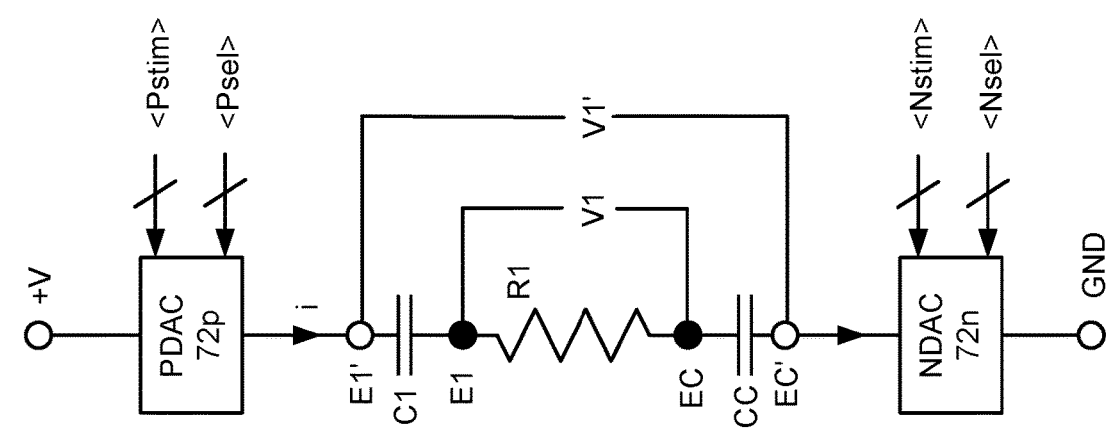
Figure 11B
Figure 11A

Connected Electrode Profile

Monopolar Impedance $\begin{bmatrix} R1 & R2 & \cdots & R31 & R32 \end{bmatrix}$ Bipolar Impedance $\begin{bmatrix} 0 & R1,2 & \cdots & R1,31 & R1,32 \\ -- & 0 & \cdots & R2,31 & R2,32 \\ \vdots & \vdots & \ddots & \vdots & \vdots \\ -- & -- & \cdots & 0 & R31,32 \\ -- & -- & \cdots & -- & 0 \end{bmatrix}$ Induced Field Potential $\begin{bmatrix} -- & V1,2 & \cdots & V1,31 & V1,32 \\ V2,1 & -- & \cdots & V2,31 & V2,32 \\ \vdots & \vdots & \ddots & \vdots & \vdots \\ V31,1 & V31,2 & \cdots & -- & V31,32 \\ V32,1 & V32,2 & \cdots & V32,31 & -- \end{bmatrix}$

*Figure 12*

SYSTEM AND METHOD FOR ENSURING A CONSISTENT CONNECTION OF ELECTRODES TO A REPLACEMENT IMPLANTABLE MEDICAL DEVICE

CROSS REFERENCE TO RELATED APPLICATIONS

This is a non-provisional application of U.S. Provisional Patent Application Ser. No. 62/568,111, filed Oct. 4, 2017, which is incorporated by reference in its entirety, and to which priority is claimed.

FIELD OF THE TECHNOLOGY

The present disclosure is related to a technique for ensuring a consistent connection of electrodes to a replacement implantable medical device to ensure consistent patient therapy.

INTRODUCTION

Neurostimulation devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows focuses on a Deep Brain Stimulation (DBS) system, such as is disclosed in U.S. Patent Application Publication No. 2013/0184794, but the disclosed techniques are applicable to other neurostimulation devices as well.

As shown in FIG. 1, a DBS system typically includes an implantable pulse generator (IPG) 10 (an implantable medical device (IMD), more generally), which includes a biocompatible device case 12 that is formed from a metallic material such as titanium. The case 12 typically comprises two components that are welded together, and it holds the circuitry and battery 14 (FIG. 2) necessary for the IPG 10 to function. The battery 14 may be either rechargeable or primary (non-rechargeable) in nature. The IPG 10 is coupled to electrodes 16 via one or more electrode leads 18 (four of which are shown). The proximal ends of the leads 18 include lead connectors 20 that are coupled to the IPG 10 at connector blocks 22 fixed in a header 24, which can comprise an epoxy for example. The lead connectors 20 are inserted into the connector blocks 22 through device connectors (e.g., ports) 8 in the header 24. Contacts in the connector blocks 22 make electrical contact with corresponding contacts on the lead connectors 20, and communicate with the circuitry inside the case 12 via feedthrough pins 26 passing through a hermetic feedthrough 28 to allow such circuitry to provide stimulation to or monitor the various electrodes 16. The feedthrough assembly 28, which is typically a glass, ceramic, or metallic material, is affixed to the case 12 at its edges to form a hermetic seal. In the illustrated system, each connector block 22 includes eight contacts and thus supports eight electrodes 16. Therefore, two four-electrode leads 18 include a single lead connector 20 that is inserted into a single connector block 22, one eight-electrode lead 18 includes a single lead connector 20 that is inserted into a single connector block 22, and one 16-electrode lead 18 includes two lead connectors 20 that are inserted into two connector blocks 22. While the illustrated system supports 32 electrodes 16 (i.e., eight electrodes for each of its four ports 8), the configuration of the connector blocks 22 and the number of supported electrodes 16 are application specific and can vary.

As shown in FIG. 2, IPG 10 contains a charging coil 30 for wireless charging of the IPG's battery 14 using an external charging device 50, assuming that battery 14 is a rechargeable battery. If IPG 10 has a primary battery 14, charging coil 30 in the IPG 10 and external charger 50 can be eliminated. IPG 10 also contains a telemetry coil antenna 32 for wirelessly communicating data with an external controller device 40, which is explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include current generation circuitry for providing stimulation pulses at one or more of the electrodes 16 and may also include telemetry modulation and demodulation circuitry for enabling bidirectional wireless communications at antenna 32, battery charging and protection circuitry coupleable to charging coil 30, DC-blocking capacitors in each of the current paths proceeding to the electrodes 16, etc. Components within the case 12 are integrated via a printed circuit board (PCB) 38.

FIG. 2 further shows the external components referenced above, which may be used to communicate with the IPG 10, in plan and cross section views. External controller 40 may be used to control and monitor the IPG 10 via a bidirectional wireless communication link 42 passing through a patient's tissue 5. For example, the external controller 40 may be used to provide or adjust a stimulation program for the IPG 10 to execute that provides stimulation to the patient. The stimulation program may specify a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated via Frequency Shift Keying (FSK) or the like, to encode transmitted data. For example, data telemetry via FSK can occur around a center frequency of fc=125 kHz, with a 129 kHz signal representing transmission of a logic '1' bit and 121 kHz representing a logic '0' bit. However, transcutaneous communications on link 42 need not be by magnetic induction, and may comprise short-range RF telemetry (e.g., Bluetooth, Bluetooth Low Energy, WiFi, Zigbee, MICS, etc.) if antennas 44 and 32 and their associated communication circuitry are so configured. The external controller 40 is generally similar to a cell phone and includes a hand-held, portable housing.

External charger 50 provides power to recharge the IPG 10's battery 14 should that battery be rechargeable. Such power transfer occurs by energizing a charging coil 54 in the external charger 50, which produces a magnetic field comprising transcutaneous link 52, which may occur with a different frequency (f2=80 kHz) than data communications on link 42. This magnetic field 52 energizes the charging coil 30 in the IPG 10, which is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

In a DBS application, as is useful in the treatment of neurological disorders such as Parkinson's disease, the IPG 10 is typically implanted under the patient's clavicle (collarbone), and the leads 18 are tunneled through the neck and between the skull and the scalp where the electrodes 16 are implanted through holes drilled in the skull in the left and right sides of the patient's brain, as shown in FIG. 3. Specifically, the electrodes 16 may be implanted in the subthalamic nucleus (STN), the pedunculopontine nucleus (PPN), or the globus pallidus internus (GPi). Stimulation therapy provided by the IPG 10 has shown promise in reducing the symptoms of neurological disorders, including rigidity, bradykinesia, tremor, gait and turning impairment, postural instability, freezing, arm swing, balance impairment, and dystonia.

After the leads are implanted, a "fitting" procedure is performed in order to customize the parameters of the stimulation provided by the IPG 10 to obtain the greatest benefit for the patient. The IPG 10 can, for example, be programmed with multiple stimulation programs that can each include multiple stimulation routines. Each stimulation routine is defined by stimulation parameters such as pulse width, stimulation amplitude, frequency, and the electrode(s) that serve as anodes and cathodes.

Referring to FIG. 4, the fitting procedure is typically performed by communicating different stimulation routines from a clinician's programmer system (CP System) 200 to the IPG 10 and observing the patient's responses to the IPG 10's execution of the different routines. For a DBS application, a clinician may observe the extent to which the current stimulation routine decreases the effects of the patient's neurological disorder (e.g., the extent to which the stimulation routine decreases the degree of tremor) as well as any side effects induced as a result of the stimulation routine. As shown, CP system 200 can comprise a computing device 202, such as a desktop, laptop, or notebook computer, a tablet, a mobile smart phone, a Personal Data Assistant (PDA)-type mobile computing device, etc. (hereinafter "CP computer"). In FIG. 5, CP computer 202 is shown as a laptop computer that includes typical computer user interface means such as a screen 204, a mouse, a keyboard, speakers, a stylus, a printer, etc., not all of which are shown for convenience.

Also shown in FIG. 4 is an accessory communication head 210 that is coupleable to a port of the CP computer 202, such as a USB port 206, and that is specific to the CP computer 202's operation as a neurostimulator controller. Communication between the CP system 200 and the IPG 10 may comprise magnetic inductive or short-range RF telemetry schemes (as described above with respect to communications between the IPG 10 and the programmer 40), and in this regard the IPG 10 and the CP computer 202 and/or the communication head 210 (which can be placed proximate to the IPG 10) may include antennas compliant with the telemetry means chosen. For example, the communication head 210 can include a coil antenna 212a, a short-range RF antenna 212b, or both. The CP computer 202 may also communicate directly with the IPG 10, for example using an integral short-range RF antenna 212b, without the use of the communication head 210.

If the CP system 200 includes a short-range RF antenna (either in CP computer 202 or communication head 210), such antenna can also be used to establish communication between the CP system 200 and other devices, and ultimately to larger communication networks such as the Internet. The CP system 200 can typically also communicate with such other networks via a wired link provided at an Ethernet or network port 208 on the CP computer 202, or with other devices or networks using other wired connections (e.g., at USB ports 206).

To test different stimulation routines during the fitting procedure, the user interfaces with a clinician programmer graphical user interface (CP GUI) 94 provided on the display 204 of the CP computer 202. As one skilled in the art understands, the CP GUI 94 can be rendered by execution of CP software 96 on the CP computer 202, which software may be stored in the CP computer 202's non-volatile memory 220. One skilled in the art will additionally recognize that execution of the CP software 96 in the CP computer 202 can be facilitated by control circuitry 222 such as a microprocessor, microcomputer, an FPGA, other digital logic structures, etc., which is capable of executing programs in a computing device. Such control circuitry 222 when executing the CP software 96 will in addition to rendering the CP GUI 94 cause telemetry circuitry in the CP computer 202 to communicate the stimulation routines to the IPG 10 using a suitable antenna 212a or 212b, either in the communication head 210 or the CP computer 202 as explained earlier. The CP software 96 enables a user to select the type of electrode lead(s) that have been implanted (e.g., from a list of leads that are configured in the software 96) and to customize the stimulation routine using the available electrodes on the implanted lead. In this way, the user can communicate different stimulation routines to the IPG 10 for execution to observe the effects of the various routines and to hone in on the appropriate settings for the patient.

SUMMARY

A system is disclosed, comprising a non-transitory computer-readable medium having instructions stored thereon to cause control circuitry in a computing device to compare a first connected electrode profile of a plurality of electrodes received from a prior implanted medical device with a second connected electrode profile of the plurality of electrodes received from a current implantable medical device; and based on the comparison, determine whether the plurality of electrodes are connected to the current implantable medical device in a similar manner as the plurality of electrodes were connected to the prior implanted medical device.

The first and second connected electrode profiles may include measurements of electrical parameters associated with the plurality of electrodes. Such electrical parameters may include a measure of impedance between one or more of the plurality of electrodes and the prior implanted medical device's case or the current implantable medical device's case, a measure of impedance between one or more pairs of the plurality of electrodes, or an electric potential that is induced at one or more of the plurality of electrodes when a current is passed through one or more of the plurality of electrodes.

The first connected electrode profile may be stored in a memory of the prior implanted medical device. The first connected electrode profile may include an average of a plurality of measurements of electrical parameters associated with the plurality of electrodes.

The computer-readable medium may further include instructions to cause the control circuitry to enable the current implantable medical device to provide stimulation when the control circuitry determines that the plurality of electrodes are connected to the current implantable medical device in the similar manner as the plurality of electrodes were connected to the prior implanted medical device. The instructions to cause the control circuitry to enable the current implantable medical device to provide stimulation may include instructions to cause the control circuitry to communicate a setting adjustment to the current implantable medical device. The instructions to cause the control circuitry to enable the current implantable medical device to provide stimulation may include instructions to cause the control circuitry to communicate stimulation parameters used by the prior implanted medical device to the current implantable medical device.

The computer-readable medium may further include instructions to cause the control circuitry to identify a mismatch between the connection of the plurality of electrodes to the current implantable medical device and the connection of the plurality of electrodes to the prior implanted medical device. The computer-readable medium may further include instructions to cause the control circuitry to present the identified mismatch to a user. The computer-readable medium may further include instructions to cause the control circuitry to adjust stimulation parameters used by the prior implanted medical device based on the identified mismatch.

The plurality of electrodes may be positioned on a plurality of electrode leads that are implanted in a patient, and each of the plurality of electrode leads may include one or more lead connectors that are each inserted into a port in the current implantable medical device. The system may include the current implantable medical device.

An implantable medical device is disclosed, comprising control circuitry that is configured to measure one or more electrical parameters associated with one or more of a plurality of electrodes that are connected to the implantable medical device; generate a replacement connected electrode profile from the measured one or more parameters; receive an initial connected electrode profile of the plurality of electrodes from a prior implanted medical device; and compare the replacement connected electrode profile with the initial connected electrode profile to determine whether the plurality of electrodes are connected to the implantable medical device in a similar manner as the plurality of electrodes were connected to the prior implanted medical device.

The one or more electrical parameters may include a measure of impedance between one or more of the plurality of electrodes and the prior implanted medical device's case or the implantable medical device's case, a measure of impedance between one or more pairs of the plurality of electrodes, or an electric potential that is induced at one or more of the plurality of electrodes when a current is passed through one or more of the plurality of electrodes.

The initial connected electrode profile may include measurements of the one or more electrical parameters associated with the one or more of the plurality of electrodes. The initial connected electrode profile may include an average of a plurality of measurements of the one or more electrical parameters associated with the one or more of the plurality of electrodes.

The control circuitry may be configured to enable the implantable medical device to provide stimulation when it is determined that the plurality of electrodes are connected to the implantable medical device in the similar manner as the plurality of electrodes were connected to the prior implanted medical device. The control circuitry may further be configured to receive stimulation parameters used by the prior implanted medical device and to provide stimulation using the received stimulation parameters.

The control circuitry may further be configured to identify a mismatch between the connection of the plurality of electrodes to the implantable medical device and the connection of the plurality of electrodes to the prior implanted medical device. The control circuitry may further be configured to receive stimulation parameters used by the prior implanted medical device and to adjust the stimulation parameters based on the identified mismatch.

The plurality of electrodes may be positioned on a plurality of electrode leads that are implanted in a patient, and each of the plurality of electrode leads may include one or more lead connectors that are each inserted into a port in the implantable medical device.

A system is disclosed, which may comprise: an external device configured to communicate with a first implantable medical device and a second implantable medical device; and a non-transitory computer-readable medium in the external device having instructions stored thereon to cause control circuitry in the external device to: compare a first connected electrode profile of a plurality of electrodes received from the first implantable medical device with a second connected electrode profile of the plurality of electrodes received from the second implantable medical device; and based on the comparison, determine whether the plurality of electrodes are connected to the second implantable medical device in a same manner as the plurality of electrodes were connected to the first implantable medical device.

The first and second connected electrode profiles may comprise measurements of electrical parameters associated with the plurality of electrodes.

The electrical parameters may comprise a measure of impedance between one or more of the plurality of electrodes and the first implantable medical device's case or the second implantable medical device's case. The electrical parameters may comprise a measure of impedance between one or more pairs of the plurality of electrodes. The electrical parameters may comprise an electric potential that is induced at one or more of the plurality of electrodes when a current is passed through one or more of the plurality of electrodes.

The computer-readable medium may further comprise instructions to cause the control circuitry to enable the second implantable medical device to provide stimulation when the control circuitry determines that the plurality of electrodes are connected to the second implantable medical device in the same manner as the plurality of electrodes were connected to the first implantable medical device. The instructions to cause the control circuitry to enable the second implantable medical device to provide stimulation may comprise instructions to cause the control circuitry to communicate stimulation parameters used by the first implantable medical device to the second implantable medical device.

The computer-readable medium further may comprise instructions to cause the control circuitry to identify a mismatch between the connection of the plurality of electrodes to the second implantable medical device and the connection of the plurality of electrodes to the first implantable medical device, wherein the external device is configured to present the identified mismatch to a user. The computer-readable medium may further comprise instructions to cause the control circuitry to adjust stimulation parameters used by the first implantable medical device based on the identified mismatch.

The system may further comprise the first and second implantable medical devices. The plurality of electrodes may be positioned on a plurality of electrode leads that are implantable in a patient, wherein each of the plurality of electrode leads comprises one or more lead connectors that are each insertable into ports in the first and second implantable medical device.

BRIEF DESCRIPTION OF THE DRAWINGS

FIG. 3 shows implantation of the IPG in a patient in a Deep Brain Stimulation (DBS) application.

FIG. 4 shows components of a clinician's programmer system, including components for communicating with an IPG.

FIGS. 11A-11C show the configuration of an IPG's current generation circuitry in order to measure monopolar impedance, bipolar impedance, and induced field potential, which may be used in generating connected electrode profiles in accordance with an aspect of the disclosure.

FIG. 12 shows an example of the measurements of electrical properties that may be included in a connected electrode profile in accordance with an aspect of the disclosure.

DETAILED DESCRIPTION

Figure 1:
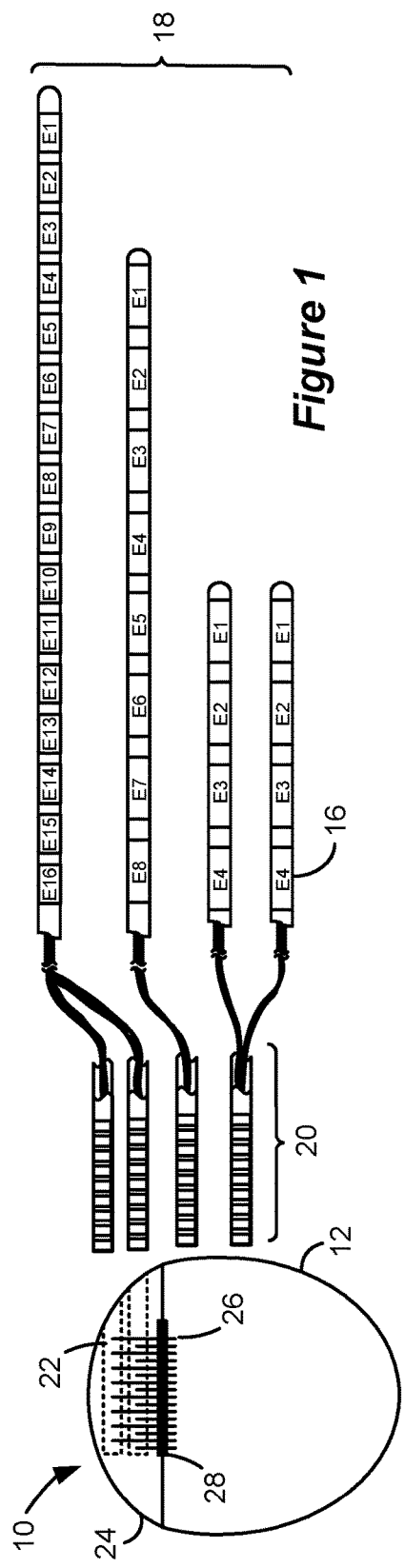
FIG. 1 shows an implantable pulse generator (IPG) with different electrode leads.
Figure 2:
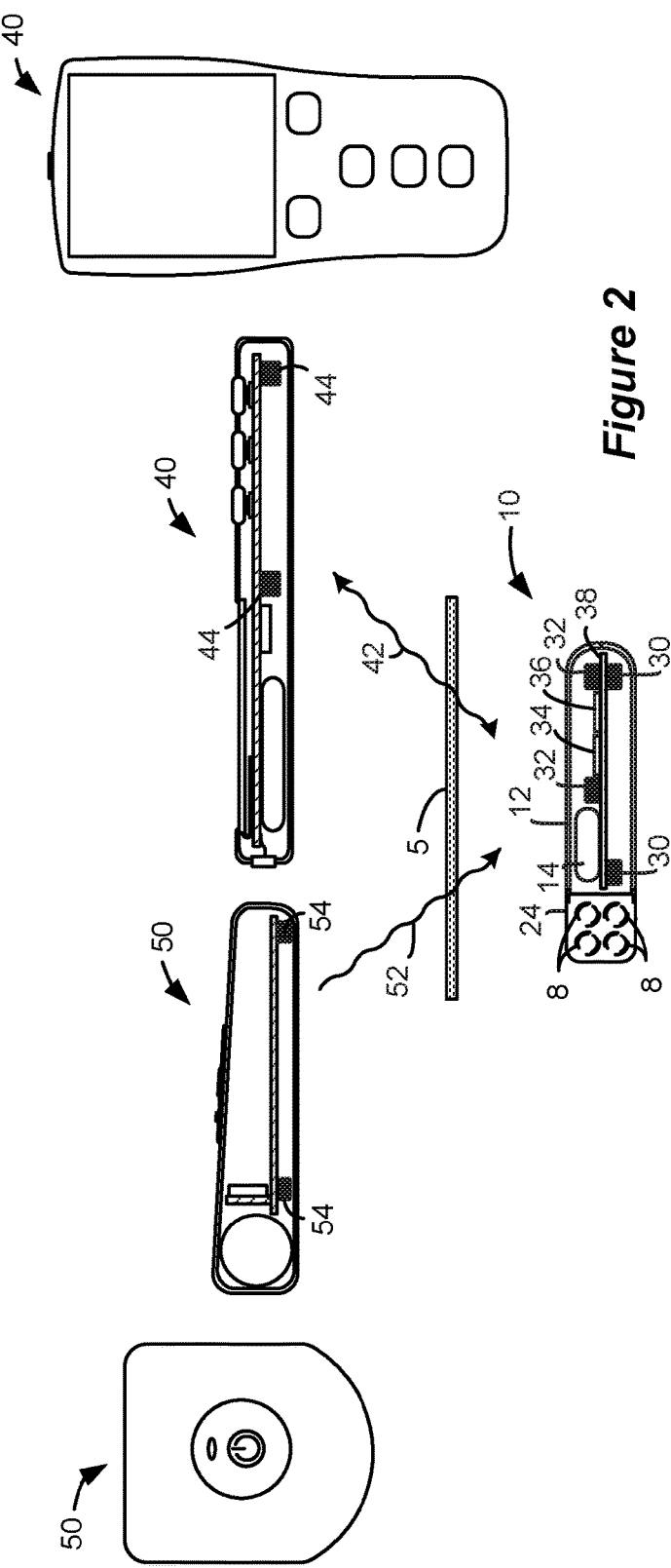
FIG. 2 shows a cross section of the IPG of FIG. 1 as implanted in a patient, as well as external devices that support the IPG, including an external charger and external controller.
Figure 5:
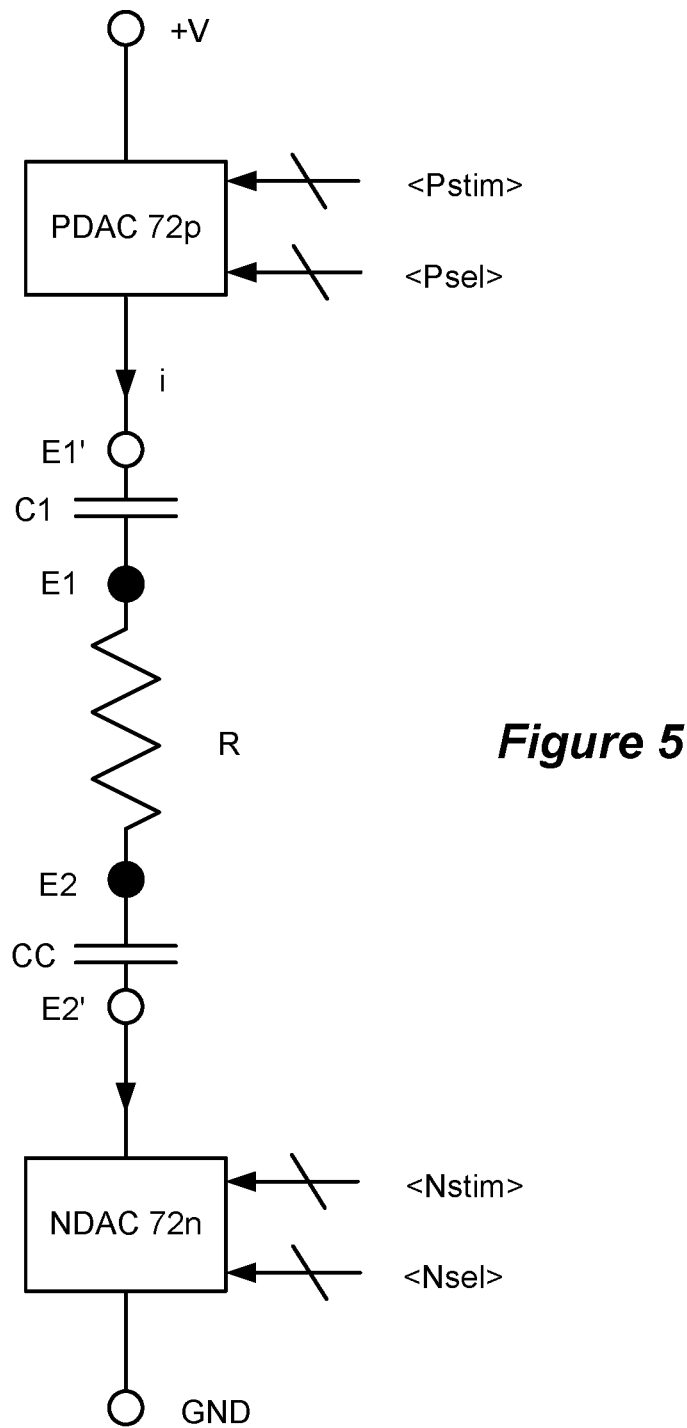
FIG. 5 shows an example of Digital-to-Analog Converter circuitry for generating electrical stimulation at selected electrodes connected to an IPG in accordance with an aspect of the disclosure.

Current generation circuitry 70 in the IPG 10 includes one or more Digital-to-Analog Converters (DACs) 72 for receiving the stimulation parameters and for forming the prescribed pulses at the selected electrodes. FIG. 5 shows a simple example of DAC circuitry 72 as used to provide a current pulse between selected electrodes E1 and E2, through a patient's tissue, R. DAC circuitry 72 as shown comprises two portions, denoted as PDAC 72p and NDAC 72n. These portions of DAC circuitry 72 are so named due to the polarity of the transistors used to build them and the polarity of the current they provide. Thus, PDAC 72p is formed from P-channel transistors and is used to source a current +I to the patient's tissue R via a selected electrode E1 operating as an anode. NDAC 72n is formed of N-channel transistors and is used to sink current −I from the patient's tissue via a selected electrode E2 operating as a cathode. It is important that current sourced to the tissue at any given time equal that sunk from the tissue to prevent charge from building in the tissue, although more than one anode electrode and more than one cathode electrode may be operable at a given time.

PDAC 72p and NDAC 72n receive digital control signals, denoted <Pstim> and <Nstim> respectively, to generate the prescribed pulses with the prescribed timing in accordance with the stimulation parameters. In the example shown, PDAC 72p and NDAC 72n comprise current sources, and in particular include current-mirrored transistors for mirroring (amplifying) a reference current Iref to produce pulses with an amplitude (A). PDAC 72p and NDAC 72n could however also comprise constant voltage sources. Control signals <Pstim> and <Nstim> also prescribe the timing of the pulses, including their duration (D) and frequency (f). The PDAC 72p and NDAC 72n along with the intervening tissue R complete a circuit between a power supply +V and ground. The compliance voltage +V is adjustable to an optimal level to ensure that current pulses of a prescribed amplitude can be produced without unnecessarily wasting IPG power.

The DAC circuitry 72 (PDAC 72p and NDAC 72n) may be dedicated at each of the electrodes, and thus may be activated only when its associated electrode is to be selected as an anode or cathode. See, e.g., U.S. Pat. No. 6,181,969. Alternatively, one or more DACs (or one or more current sources within a DAC) may be distributed to a selected electrode by a switch matrix (not shown), in which case optional control signals <Psel> and <Nsel> would be used to control the switch matrix and establish the connection between the selected electrode and the PDAC 72p or NDAC 72n. See, e.g., U.S. Pat. No. 8,606,362. DAC circuitry 72 may also use a combination of these dedicated and distributed approaches. See, e.g., U.S. Pat. No. 8,620,436.

As shown, the current I is routed from the PDAC 72p to electrode node E1' (a node in the IPG 10's current generation circuitry 70 that is coupled to electrode E1 and is differentiated from electrode E1 by the prime designator). From electrode node E1', the current I flows through a blocking capacitor C1 to the electrode E1. The NDAC 72n pulls the current I through the patient's tissue R from electrode E2 through the blocking capacitor C2 and to the electrode node E2'.

Figure 6:
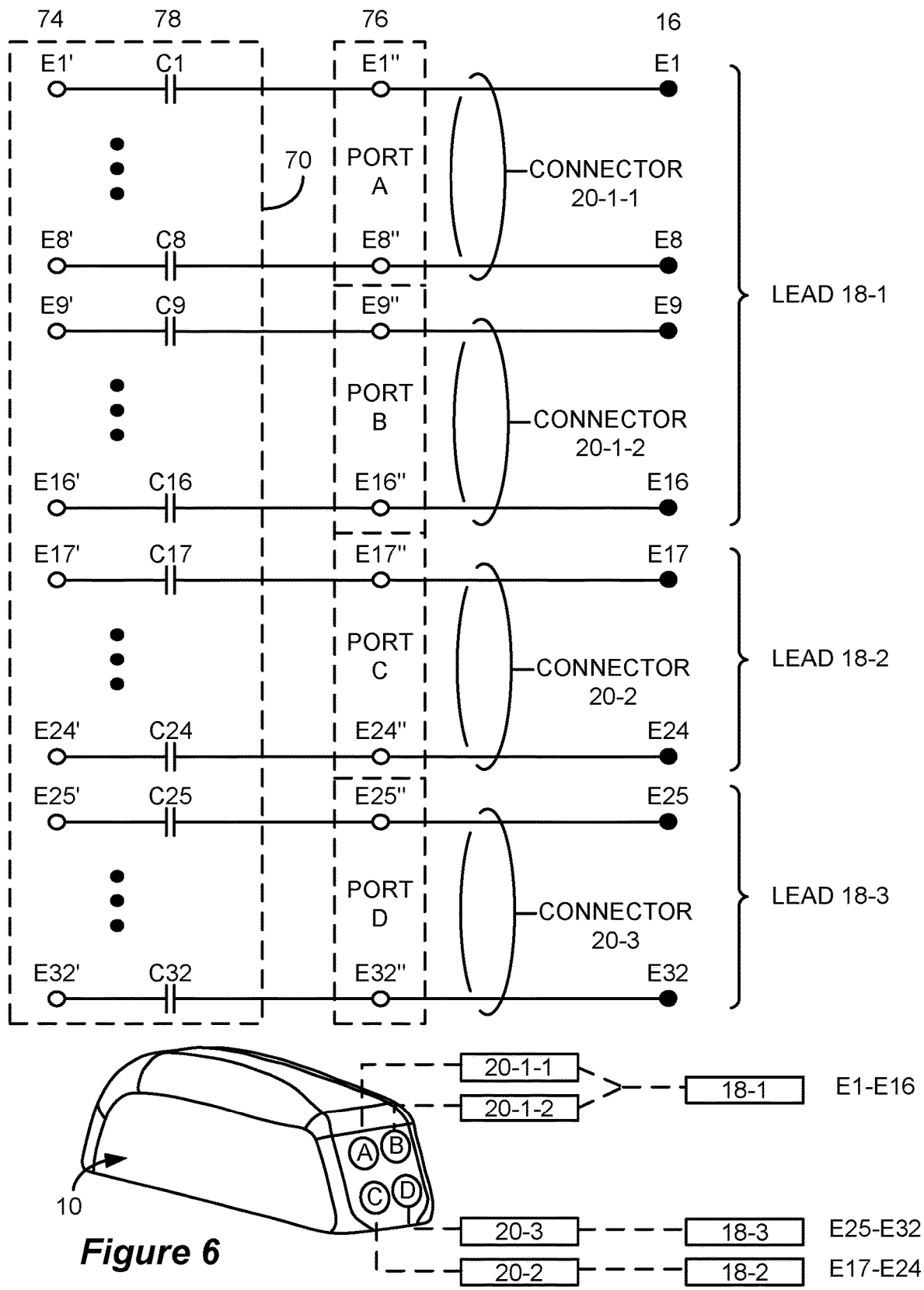
FIG. 6 shows an example of the physical connection between electrode nodes in an IPG's current generation circuitry and corresponding electrodes in accordance with an aspect of the disclosure.

FIG. 6 illustrates an example of the physical connection of the electrode nodes 74 in the IPG 10's current generation circuitry 70 with the lead-based electrodes 16. In the illustrated example, the IPG 10 supports 32 lead-based electrodes 16 although the number of electrodes can vary. Each electrode node 74 is coupled to a corresponding contact 76 in one of the IPG 10's connector blocks 22 through a blocking capacitor 78. For example, electrode node E1' is coupled to contact E1" in the connector block labeled as port A through blocking capacitor C1. Each electrode 16 is coupled to a contact in its lead connector 20, which lead connector contact is coupled to a corresponding contact 76 in the connector block 22 in which the lead connector 20 is inserted.

In the example shown, three different leads are coupled to the IPG 10: a 16-electrode lead 18-1 and two eight-electrode leads 18-2 and 18-3. Lead 18-1's lead connectors 20-1-1 and 20-1-2 are inserted into the connector blocks 22 associated with ports A and B, respectively, lead 18-2's lead connector 20-2 is inserted into the connector block 22 associated with port C, and lead 18-3's lead connector 20-3 is inserted into the connector block 22 associated with port D. Thus, lead 18-1's electrodes are coupled to electrode nodes E1'-E16', lead 18-2's electrodes are coupled to electrode nodes E17'-E24', and lead 18-3's electrodes are coupled to electrode nodes E25'-E32'. Accordingly, stimulation supplied to electrode nodes E1'-E32' in accordance with the defined stimulation parameters is routed to corresponding electrodes E1-E32. The illustrated electrode arrangement is provided as an example, and, as noted above, the number of electrodes and the configuration of the current generation circuitry 70 and connector blocks 22 is application-specific and can vary between different IPGs 10.

Figure 7:
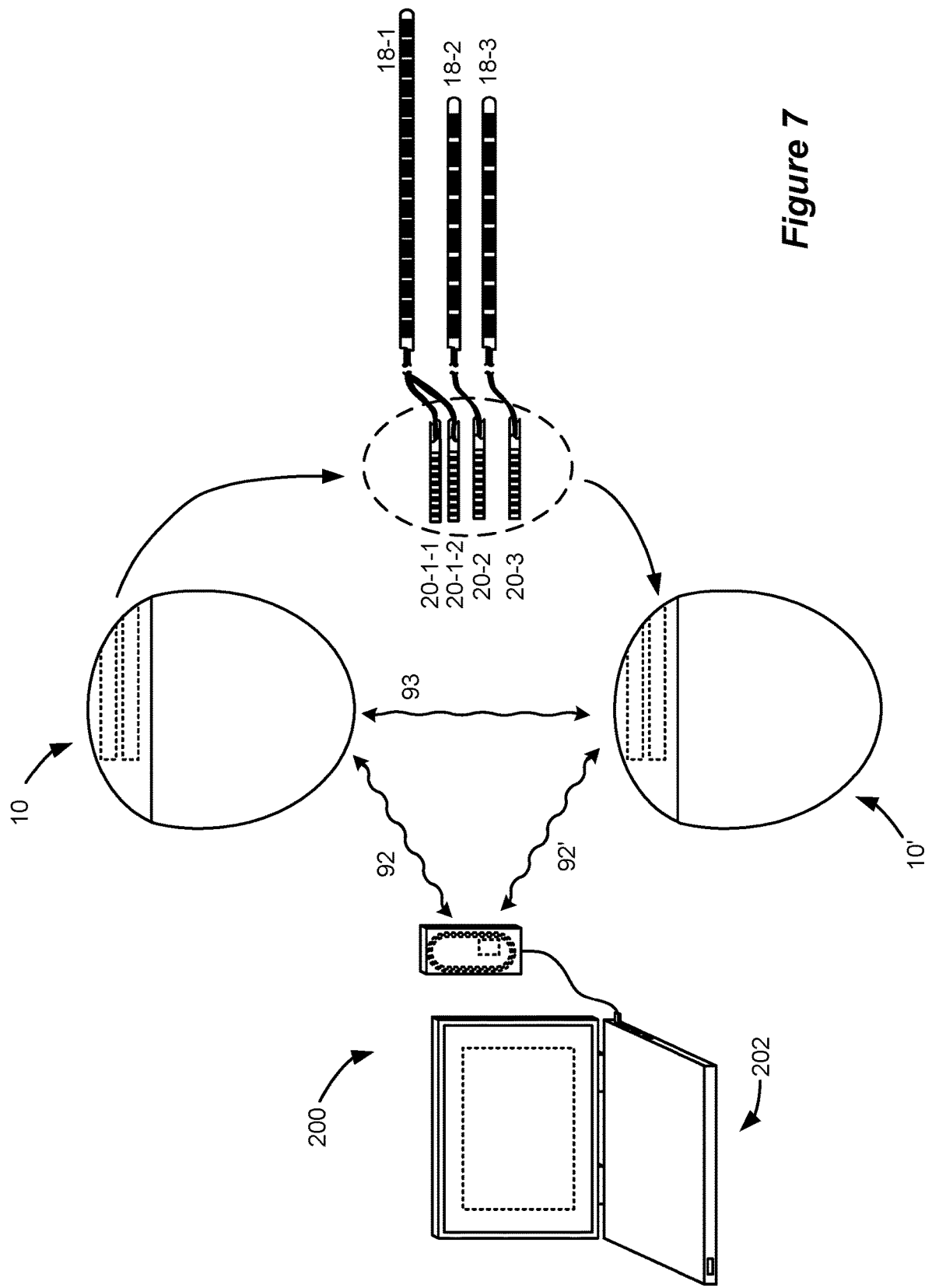
FIG. 7 shows an example of the replacement of an IPG with a new IPG and the reconnection of previously-implanted electrode leads in accordance with an aspect of the disclosure.

A typical IPG 10 used in a DBS application may have a two to three year replacement interval. Given the seriousness of the procedure for lead implantation in the brain, when the IPG 10 is replaced, the initial leads 18 are typically reused with the replacement IPG 10'. As illustrated in FIG. 7, this process typically involves removing the lead connectors 20 from the connector blocks 22 in the IPG 10 and inserting the lead connectors 20 in the connector blocks 22 in the replacement IPG 10'. If the replacement IPG 10' does not support the lead connectors 20 of the implanted leads 18 (e.g., the replacement IPG 10' is a newer generation device with a different type of connector block 22 or is manufactured by a different manufacturer than the IPG 10), an adapter may be utilized to convert the lead connectors 20 to the type of lead connector that is supported by the replacement IPG 10'. The IPG 10 and the replacement IPG 10' may also be referred to as the initial or prior IPG 10 and the current IPG 10', respectively. In addition, both the IPG 10 and the replacement IPG 10' may be referred to as either an implanted (or previously implanted) or an implantable medical device.

It is desirable to transfer the stimulation parameters that define the therapy that was being provided by the IPG 10 to the replacement IPG 10' at the time of replacement such that consistent therapy can be provided. The stimulation parameters are stored in a memory in the IPG 10 and can be transferred to an external device such as the CP computer 202 via communication link 92 and relayed to the replacement IPG 10' via the communication link 92'. The stimulation parameters may alternatively be communicated directly from the IPG 10 to the replacement IPG 10' via the IPG-to-IPG communication link 93. In another embodiment, the stimulation parameters may be stored in a patient profile on an external device such as the CP computer 202 and may be communicated directly to the replacement IPG 10' via the communication link 92'. Communications on links 92, 92', and 93 can occur via magnetic inductive coupling or short-range RF telemetry as described above.

Using the stimulation parameters received from the IPG 10, the replacement IPG 10' can provide the same therapy that was being provided by the IPG 10. It is obviously important, though, that stimulation be directed to the same electrodes that were used by the IPG 10. In this regard, it is important to understand how the electrodes 16 are connected to the current generation circuitry in the replacement IPG 10'.

Figure 8:
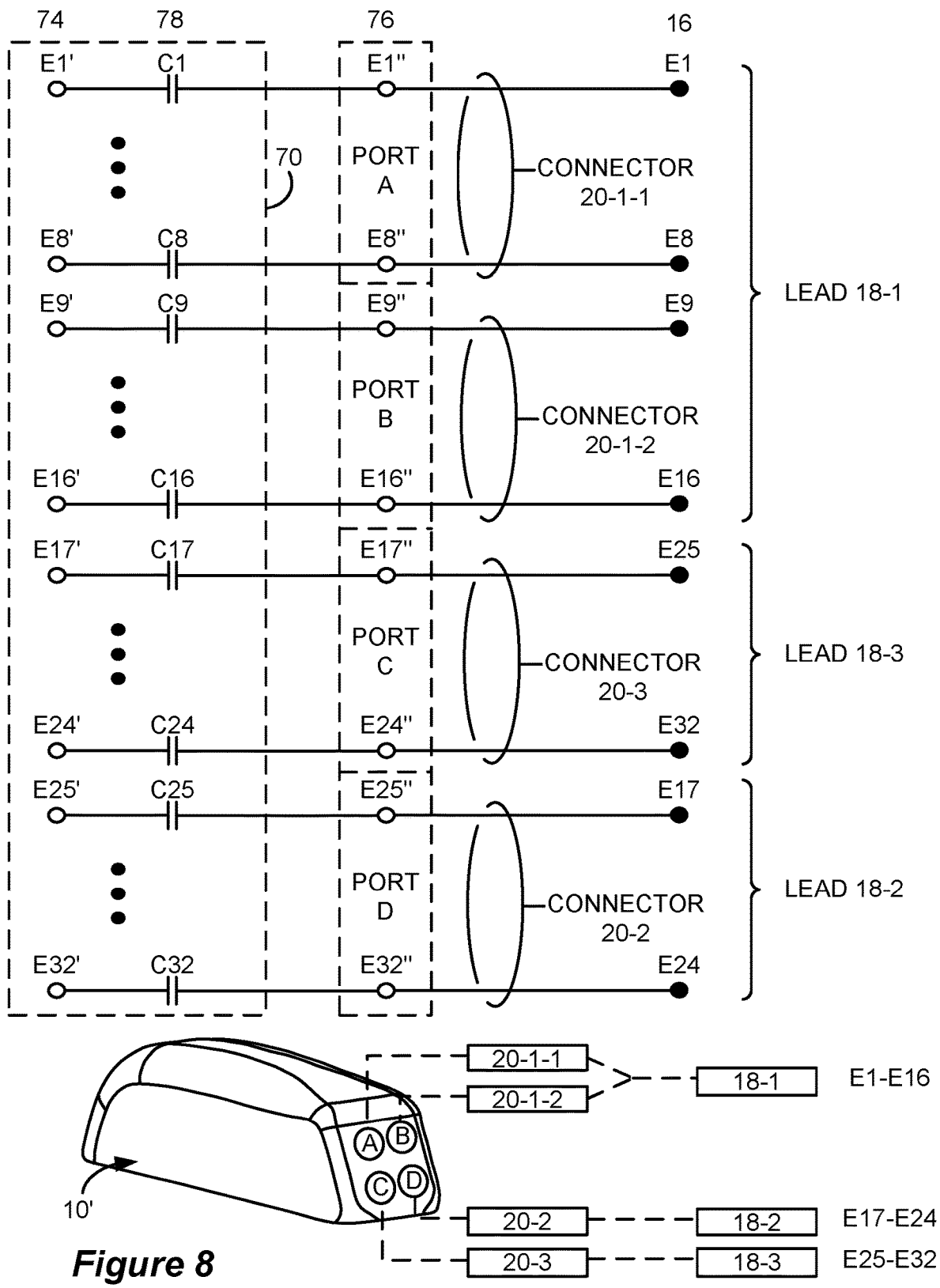
FIGS. 8-10 show examples of the electrode leads shown in FIG. 7 being connected to a replacement IPG in a manner that is not consistent with their connection to the IPG shown in FIG. 7 in accordance with an aspect of the disclosure.

FIG. 8 illustrates an example replacement IPG 10' that has the same electrode node 74 to contact 76 configuration as the IPG 10 shown in FIG. 6. However, at the time the replacement IPG 10' is implanted, the lead connectors 20-2 and 20-3 are swapped as compared to their previous connection to IPG 10. Specifically, connector 20-2 is inserted in port D (as opposed to port C) and connector 20-3 is inserted in port C (as opposed to port D). As a result, if the transferred stimulation parameters are utilized in IPG 10', stimulation that is intended for electrodes E17-E24 is routed to electrodes E25-E32 and stimulation intended for electrodes E25-E32 is routed to electrodes E17-E24. These electrodes, which are positioned on different leads 18, may be positioned in very different locations in the brain. As a result, the stimulation parameters that provided effective stimulation in IPG 10 may be entirely ineffective given the inconsistent connection of the leads 18 to IPG 10' or, even worse, may cause dangerous side effects. While inconsistent lead connector insertion in a replacement IPG 10' can occur as a result of user error even when the replacement IPG 10' matches the replaced IPG 10, the problem is exacerbated when the replacement IPG 10' is of a different type than the replaced IPG 10.

Figure 9:
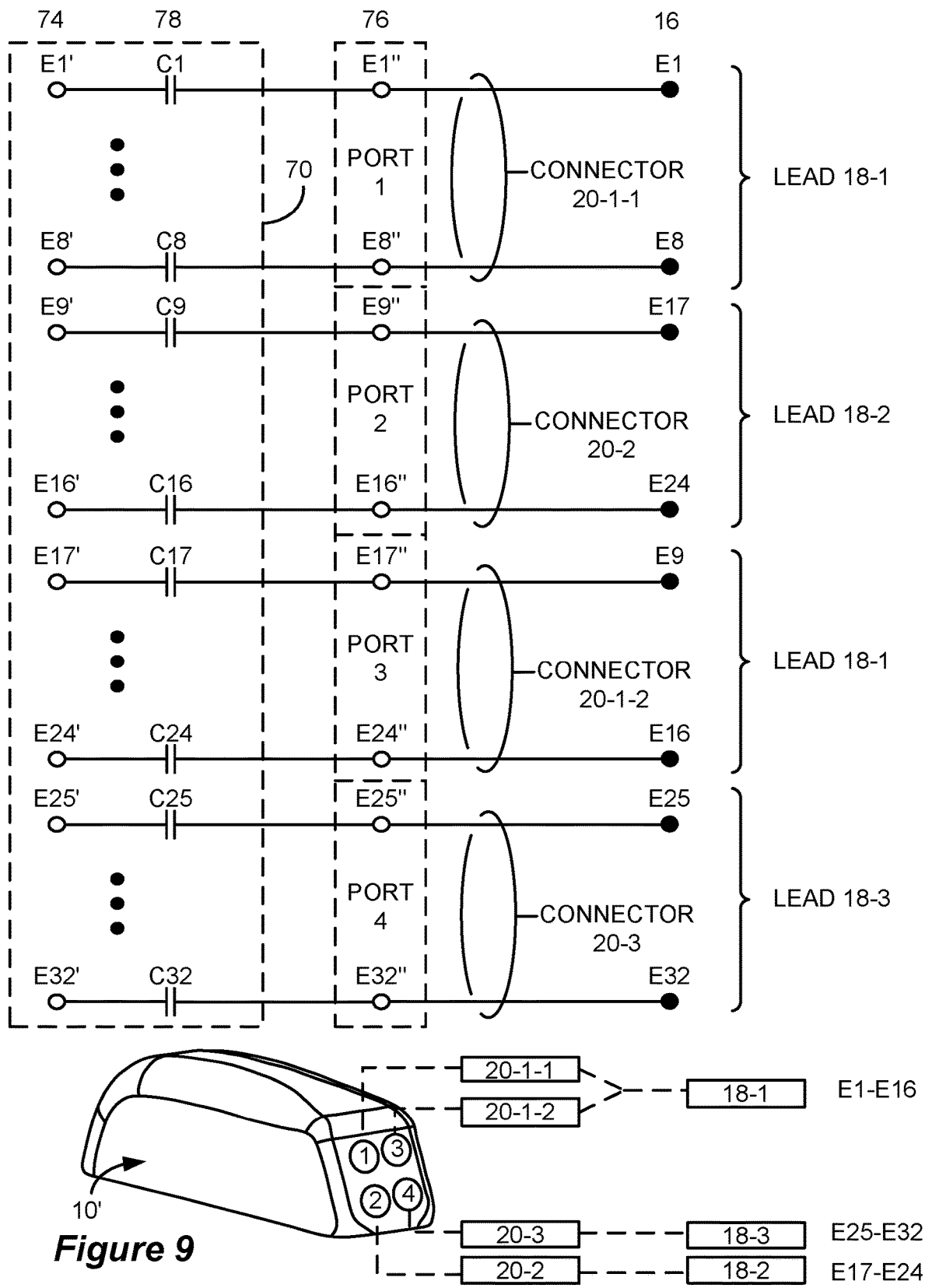

FIG. 9 illustrates an example replacement IPG 10' in which the lead ports 8 are differently labeled than in the IPG 10. Specifically, the lead ports 8 in the replacement IPG 10' are labeled 1-4 as opposed to the A-D labels in the IPG 10. Moreover, the layout of the ports 8 in the IPG 10' doesn't match that of the IPG 10 (i.e., port 3 is in the position of port B and port 2 is in the position of port C). Consequently, the lead connectors 20-1-2 and 20-2 are swapped as compared to the correct connection. As a result, if the transferred stimulation parameters are utilized in IPG 10', stimulation that is intended for electrodes E9-E16 is routed to electrodes E17-E24 and stimulation intended for electrodes E17-E24 is routed to electrodes E9-E16. As described above, this can have undesirable consequences.

Figure 10:
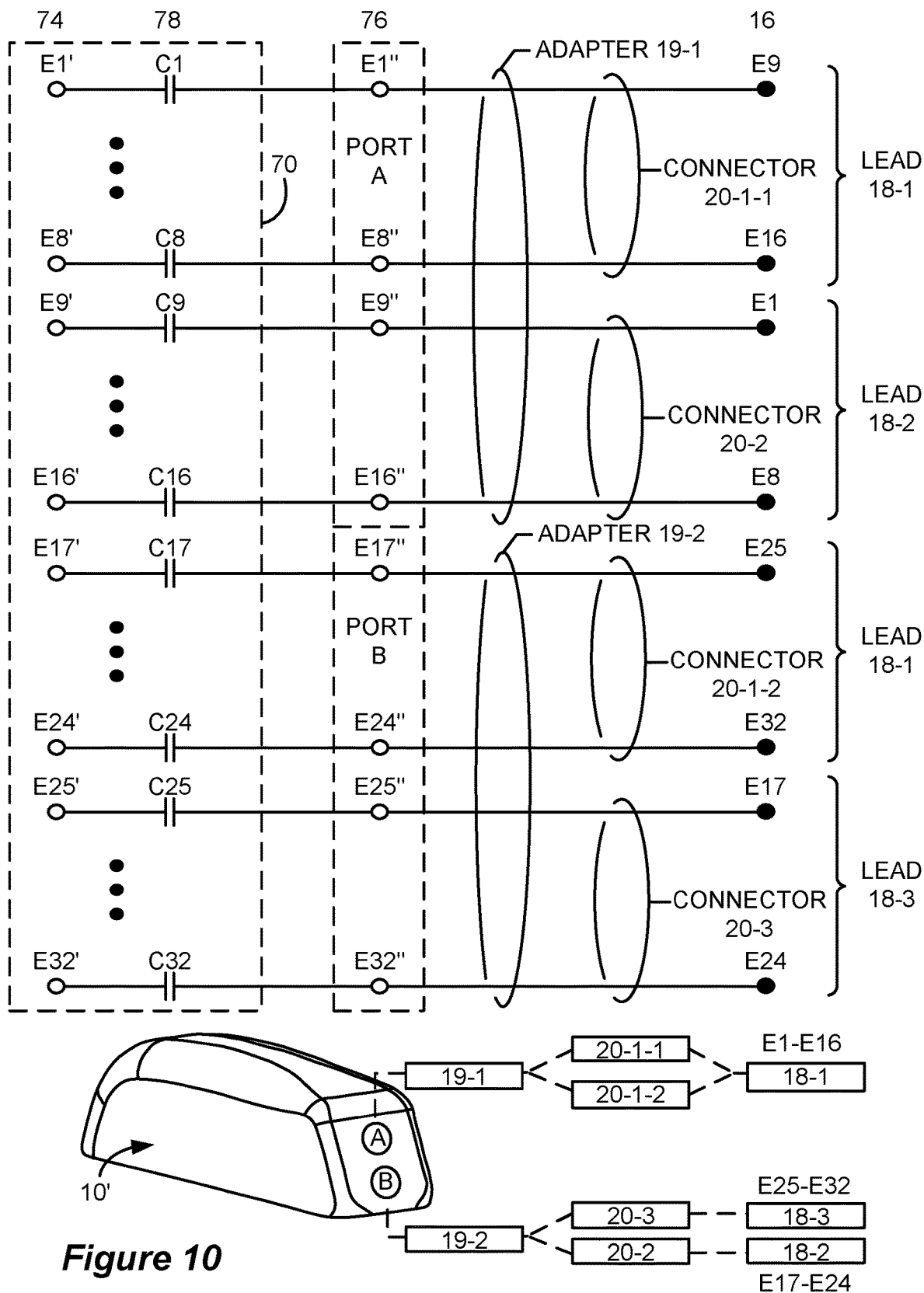

FIG. 10 illustrates an example replacement IPG 10' having two 16-contact connector blocks 22' as opposed to four eight-contact connector blocks 22. Due to the different connector block arrangement, adapters 19 are used to convert the lead connectors 20 to the lead connectors 20' that are compliant with the connector blocks 22'. Due to the internal wiring in the adapters 19, the lead connectors 20 in each adapter are swapped as compared to the correct connection. As a result, if the transferred stimulation parameters are utilized in IPG 10', stimulation that is intended for electrodes E1-E8 is routed to electrodes E9-E16 and stimulation intended for electrodes E9-E16 is routed to electrodes E1-E8. Similarly, stimulation that is intended for electrodes E17-E24 is routed to electrodes E25-E32 and stimulation intended for electrodes E25-E32 is routed to electrodes E17-E24. Again, this can have undesirable consequences.

As can be seen from these examples, when stimulation parameters from an IPG 10 are used to mimic the stimulation in a replacement IPG 10', it is important to verify that the connection of the leads 18 to the IPG 10' is consistent with the stimulation parameters, or, alternatively, to alter the stimulation parameters based on the connection of the leads 18 to the replacement IPG 10'. The inventors have determined that various electrical parameters can be measured at the electrode nodes 74 in the IPG 10 to create an initial connected electrode profile of the connected electrodes. Corresponding measurements can be taken in the replacement IPG 10' to create a replacement connected electrode profile of its connected electrodes. The initial connected electrode profile and the replacement connected electrode profile can then be compared to determine whether the electrodes 16 have been connected to the replacement IPG 10' in a manner that is consistent with their connection to the IPG 10.

FIGS. 11A-11C illustrate DAC circuitry as configured to make different types of measurements that can be included in the connected electrode profiles. The DAC circuitry in these illustrations can be implemented in the same or similar manner in both the initial IPG 10 and the replacement IPG 10' and therefore reference to the IPG 10 applies equally to the IPG 10'. FIG. 11A shows the DAC circuitry 72 as configured to provide a current pulse between selected electrode E1 and the IPG 10's case 12, which can be configured as an electrode. Measurement circuitry in the IPG 10 is configured to measure the voltage between selected nodes. In FIG. 11A, the measurement circuitry is configured such that the voltage V1' between electrode nodes E1' and EC' is measured. U.S. Pat. No. 9,061,140, which is incorporated herein by reference in its entirety, describes measurement circuitry and a corresponding measurement technique that can be utilized to remove the voltage across the blocking capacitors (C1 and CC) from the V1' measurement, thus providing the voltage V1 between electrodes E1 and EC. Using the measured voltage V1 and the known current I, the impedance R1 between electrodes E1 and EC can be calculated as R1=V1/I. While the impedance can be converted to units of resistance, a common current can be utilized for all measurements, and the measure of impedance of different electrodes can be specified in terms of the measured voltage drop. This type of measurement of the impedance between a lead-based electrode 16 and the IPG 10's case can be described as monopolar impedance, and such monopolar impedance measurements can be obtained for each of the lead-based electrodes 16 (preferably using a common stimulation current or voltage for all measurements). The monopolar impedance measurement for a particular electrode is generally a function of the properties of the electrode (e.g., the electrode's physical size, etc.) and the electrical properties of the tissue between the electrode and the IPG's case. Because these properties vary from electrode to electrode, monopolar impedance measurements can form a portion of the connected electrode profiles that enable the different electrodes to be distinguished from each other.

FIG. 11B shows DAC circuitry 72 as configured to provide a current pulse between selected electrodes E1 and E2, through the patient's tissue, R. This arrangement is substantially similar to the arrangement shown in FIG. 11A except a lead-based electrode 16 is selected to operate as the cathode rather than the IPG 10's case 12. The impedance measurement can be obtained in the same manner as described above by selecting the active anode and cathode electrode nodes in the measurement circuitry. In the specific example illustrated in FIG. 11B, the impedance R1,2 is measured between electrodes E1 and E2. As with monopolar impedance measurements, while the impedance can be converted to units of resistance, a common current can be utilized for all measurements, and the measure of impedance between different electrodes can be specified in terms of the measured voltage drop. Such bipolar impedance measurements can be collected for each pair of electrodes (preferably using a common current or voltage amplitude for each). In one embodiment, the impedance between a pair of electrodes can be assumed to be equal regardless of the polarity of the electrodes (i.e., regardless of which electrode acts as the cathode and which acts as the anode), thus reducing the number of impedance measurements by one-half. Alternatively, the bipolar impedance measurements can be collected for both polarity arrangements for each electrode pair. The bipolar impedance measurement for a particular electrode pair is generally a function of the properties of the electrodes (e.g., the electrodes' physical size, etc.), the electrical properties of the tissue between the electrodes, and the distance between the electrodes (which has much more bearing on the bipolar impedance measurement than the distance between any electrode and the IPG 10's case in the monopolar impedance measurements). Because these properties vary for different electrode pairs, bipolar impedance measurements can form another portion of the connected electrode profiles that enable the different electrodes to be distinguished from each other.

FIG. 11C shows DAC circuitry 72 as configured to provide a current pulse between electrode E1 and the IPG 10's case 12 (EC) in the same manner as described above with respect to FIG. 11A. However, in FIG. 11C, the measurement circuitry is configured to measure the voltage at other electrodes (e.g., electrode E4 in the configuration illustrated in FIG. 11C) including those that are not used for stimulation. During a stimulation pulse (between E1 and EC in the configuration illustrated in FIG. 11C), an electric field 150 is generated in the patient's tissue, R. The field 150 is strongest nearest to the stimulating electrode, and its strength decreases with increasing distance from the stimulating electrode. As a result, the measurement of a voltage between an electrode (e.g., electrode E4) and a reference voltage (e.g., a ground reference) provides an indication of the distance between the stimulating electrode and the electrode at which the measurement was taken. In FIG. 11C, the voltage at electrode E4 couples through the capacitor C4, and the induced voltage measurement V1,4 is measured between the electrode node E4' and a ground reference node. Induced voltage measurements can be obtained for each of the electrodes (e.g., at each of the electrodes when stimulation is between electrode E1 and the case 12, at each of the electrodes when stimulation is between electrode E2 and the case 12, and so on). While it is not strictly necessary, in a preferred embodiment, the IPG 10's case 12 is selected as one of the stimulating electrodes and the selected amplitude of stimulation is held constant for the collection of all of the induced field potential measurements. Selection of the case 12 as one of the stimulating electrodes provides a cleaner induced field potential data set as its distance from the lead-based electrodes 16 avoids any interference that may otherwise be present were two lead-based electrodes 16 used as stimulating electrodes. The induced field potential measurements can be obtained at any point during the stimulation pulse. Because the voltage that is induced at an electrode differs as a result of its relationship to the stimulating electrode, such induced field potential measurements can form yet another portion of the connected electrode profiles that enable the different electrodes to be distinguished from each other.

FIG. 12 illustrates an example of a connected electrode profile. In the illustrated example, the connected electrode profile includes monopolar impedance, bipolar impedance, and induced field potential measurements for the electrodes connected to an IPG 10. The monopolar impedance data is illustrated as a 1×n matrix of Rx measurements where n is the number of electrodes (32 in the example shown) and Rx is the measured monopolar impedance for electrode x. The bipolar impedance data is illustrated as a n×n matrix with Rx,y measurements in the upper-right triangle of the matrix where $R_{x,y}$ is the measured bipolar impedance between electrode x acting as an anode and electrode y acting as a cathode. The measurements on the matrix diagonal are listed as '0' because they correspond to the intersection of a single electrode operating as an anode and a cathode. The measurements in the lower-left triangle are not recorded in the illustrated bipolar impedance measurements because they correspond to a measurement in the upper-right triangle but with the same pair of electrodes operating at different polarities. While this approach reduces the number of measurements that must be taken and the amount of data to be stored as part of the profile, in another embodiment, bipolar impedance measurements could be recorded for both polarities for each pair of electrodes. The induced field potential data is illustrated as a n×n matrix of $V_{x,y}$ measurements where $V_{x,y}$ is the voltage induced at electrode y when electrode x acts as a stimulating electrode. The measurements on the matrix diagonal are not recorded because they correspond to the voltage at a particular electrode when the electrode itself operates as the stimulating electrode, although these measurements could be recorded in another embodiment. Unlike the bipolar impedance data, the induced field potential data includes two measurements for each pair of electrodes (i.e., measurements are recorded for both the field induced at electrode a when electrode b is stimulated and the field induced at electrode b when electrode a is stimulated), but in another embodiment a single measurement could be taken for each pair of electrodes. While the illustrated example of the connected electrode profile includes monopolar impedance, bipolar impedance, and induced field potential measurements, the connected electrode profile can include more or less data than what is shown. For example, the connected electrode profile could include measurements of additional electrical parameters or it could include some subset of the measurements illustrated in FIG. 12.

In one embodiment, the measurements comprising the connected electrode profile may be routinely collected by the IPG 10 while the IPG 10 is implanted in the patient. For example, the electrical parameters of the electrodes that make up the connected electrode profile may be measured every hour, every eight hours, every day, every five days, or at any selected measurement interval. When the parameters are measured, the collected electrode profile is updated. For example, in one embodiment, the profile may comprise the most recent measurements of the electrical parameters. In another embodiment, the profile may comprise an average of a specified number of the most recent measurements (e.g., the five most recent measurements, the ten most recent measurements, the measurements taken within the last 30 days, etc.). When the connected electrode profile comprises an average of recent measurements, a statistical analysis may be utilized to determine which measurements should be included in the average. For example, a set of measurements that appears to contain a large number of statistical anomalies may not be included in the average that makes up the profile. Regardless of the manner in which the connected electrode profile is updated, it is stored within a memory in the IPG 10. While the electrical parameters that make up the connected electrode profile may change gradually over time such as during the formation of scar tissue around the leads 18, the electrical parameters are generally stable during any brief period and thus provide a way to distinguish the different electrodes from each other. It is important to note that the electrode identifiers in the profiles correspond to electrode node identifiers, which electrode node identifiers correspond to the stimulation parameters. For example, measurements labeled as E1 in the profiles correspond to measurements for the electrode that is connected to electrode node E1', which electrode node E1' receives stimulation directed to electrode E1 in the stimulation parameters.

Figure 13:
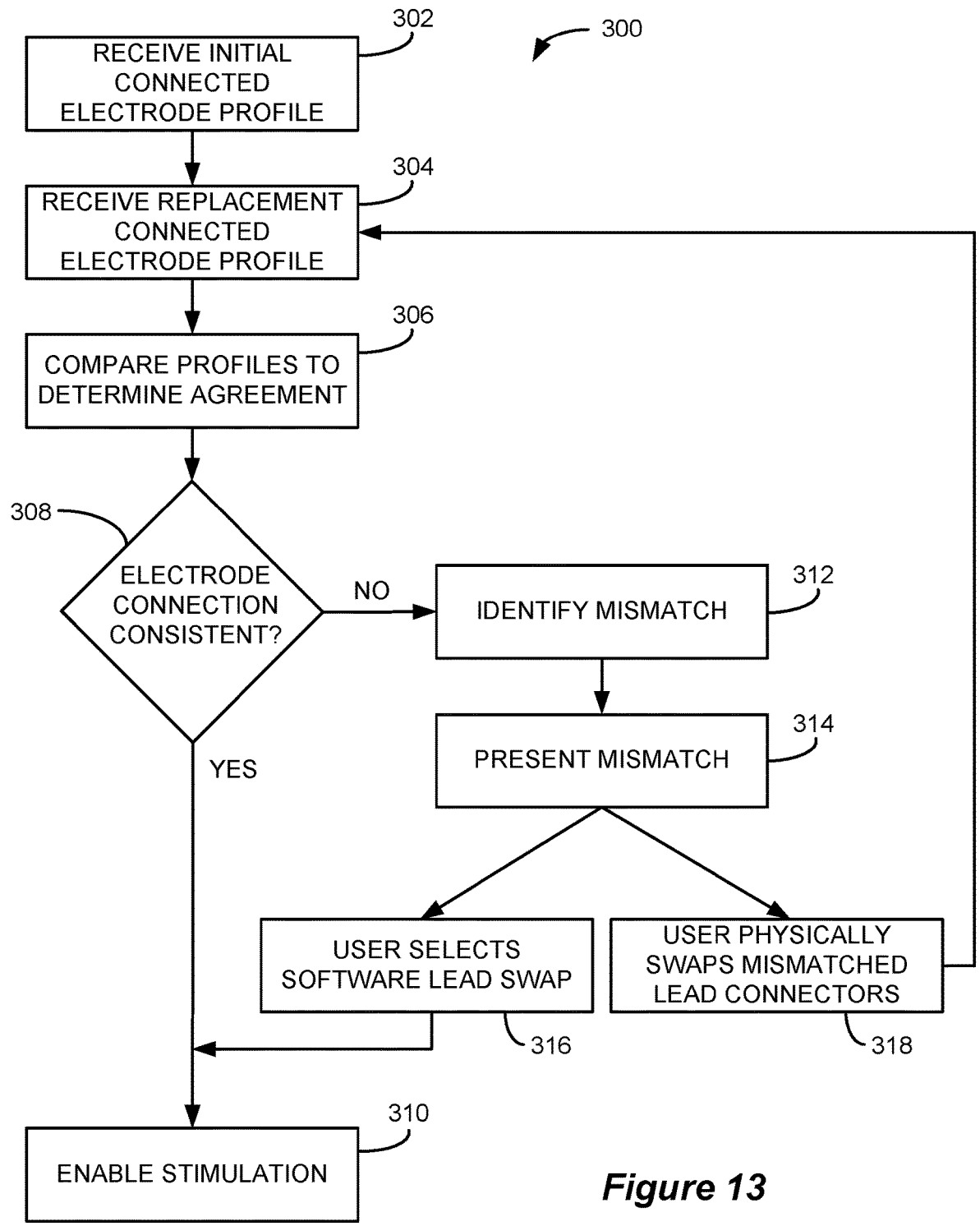
FIG. 13 is a flowchart that shows a process for evaluating the connection of electrodes in a replacement IPG in the context of the use of stimulation parameters from a previously-implanted IPG in accordance with an aspect of the disclosure.

FIG. 13 is a flowchart that shows a process 300 for evaluating the connection of electrodes in a replacement IPG 10' in the context of the use of stimulation parameters from an initial IPG 10. The process 300 is performed on an external device such as the CP computer 202, and it may be incorporated into CP software 96. Initially, the initial connected electrode profile is received from the initial IPG 10 (302). As described above, the initial connected electrode profile may be stored in a memory in the IPG 10. The initial connected electrode profile may be received in response to a request that is sent from the CP computer 202 to the IPG 10 (e.g., via communication link 92). Such a request may be generated as part of a process that is performed prior to, or immediately after, explantation of the IPG 10. The replacement connected electrode profile is then received from the replacement IPG 10' (304) after the leads 18 are connected to the replacement IPG 10'. In one embodiment, the measurements that comprise the replacement connected electrode profile may be made by the replacement IPG 10' as part of its initialization process (i.e., without a request from the external device). In another embodiment, the measurements that comprise the replacement connected electrode profile may be made in response to a request that is sent from the CP computer 202 to the IPG 10' (e.g., via communication link 92'). Such a request may specify the information that should be included in the replacement connected electrode profile, which may be determined based on the information in the initial connected electrode profile. For example, if the initial connected electrode profile includes measurements for a first electrical parameter but omits measurements for a second electrical parameter, the request can specify that measurements should be provided for the first electrical parameter but not the second electrical parameter. While the initial connected electrode profile may include an average of measurements that are taken over a period of time as described above, the replacement connected electrode profile will typically comprise a single set of measurements or an average of a relatively limited number of sets of measurements.

The initial and replacement connected electrode profiles are then compared to evaluate their agreement (306). The profiles may be compared by computing one or more measures of their correlation. For example, corresponding portions of the profiles (e.g., portions corresponding to the same groups of electrode nodes) may be analyzed using a function such as the Pearson Correlation function. For example, the Pearson coefficient may be calculated for the induced field potential measurements associated with corresponding electrode nodes or groups of electrode nodes in the profiles. Because agreement between the profiles may be evaluated for various subgroups of the profiles, the measure(s) of agreement may be expressed as a matrix. For example, the calculated measure(s) of agreement between the profiles may be a matrix of Pearson coefficient values. While Pearson correlation coefficient values are described, other statistical measures of agreement may also be employed as will be understood. For example, the agreement values may be calculated as a matrix of raw comparisons of corresponding values between the profiles (e.g., the ratio of the difference between corresponding values to the value in the initial connected electrode profile). It will be understood that essentially any statistical measures that can be used to evaluate agreement between datasets can also be employed to evaluate the agreement between the profiles.

Regardless of their specific form, the agreement measure(s) are evaluated to determine if the profiles indicate that the electrodes are connected to the replacement IPG 10' in a similar manner in which they were connected to the IPG 10 (308). The electrodes are connected to the replacement IPG 10' in a similar manner as they were connected to the IPG 10 if stimulation parameters used by the IPG 10 would result in stimulation being directed to the same electrodes in the IPG 10' as it was in the IPG 10. In one embodiment, the measure(s) of agreement are compared to a threshold to determine whether the electrodes are connected in the similar manner. The threshold may be selectable by a user such as through the CP software 96. By way of example, Pearson coefficient values would be expected to be very near 1 if the electrodes are connected to the replacement IPG 10' in a similar manner as the IPG 10. In one embodiment, the average and standard deviation of the agreement measures are evaluated to determine whether the electrodes are connected to the replacement IPG 10' in a similar manner in which they were connected to the IPG 10. For example, the electrodes may be determined to be connected to the replacement IPG 10' in a similar manner in which they were connected to the IPG 10 if the average of multiple agreement values exceeds an agreement threshold and the standard deviation of the multiple agreement thresholds is less than a variation threshold. The agreement measure(s) may also be utilized to determine a confidence value that is indicative of the level of confidence that the electrodes are connected to the replacement IPG 10' in a similar manner in which they were connected to the IPG 10.

If it is determined that the electrodes are connected to the replacement IPG 10' in a similar manner in which they were connected to the IPG 10 (the "Yes" prong of 308), stimulation is enabled for the IPG 10' using the stimulation parameters from the IPG 10 (310). Stimulation may be enabled by providing the stimulation parameters from the IPG 10 to the replacement IPG 10' (e.g., via communication link 92'). Stimulation may also be enabled by communicating an adjustment to a setting in the replacement IPG 10' that prevents stimulation using stimulation parameters transferred from the IPG 10 until the process 300 is successfully performed. In addition to enabling stimulation, the process 300 may notify the user that the electrodes were determined to be connected to the IPG 10' in a similar manner as they were connected to the IPG 10. For example, the process 300 may present the determination and the determined confidence value via the user interface 94.

If it is determined that the electrodes are connected to the replacement IPG 10' in a different manner than they were connected to the IPG 10 (the "No" prong of 308), the mismatch is identified (312). The mismatch between the connection of electrodes to the initial IPG 10 and the connection of electrodes to the IPG 10' can be identified from the agreement values. For example, as illustrated above, mismatch typically occurs across groups of electrodes such as when the lead connectors 20 corresponding to those groups of electrodes are swapped. The agreement values will typically indicate disagreement within sections of the profiles corresponding to these groups of electrodes. The identification of the mismatch can utilize knowledge of the types of connected electrode leads, and, more specifically, knowledge of those lead types' lead connectors 20. This type of lead information is typically entered in the CP software 96 and it is useful in verifying electrode groups (e.g., groups that may have been swapped).

An assumed mismatch can be verified by swapping the values in the replacement connected electrode profile based on the assumed mismatch and recalculating the agreement values. For example, if it is assumed that electrodes E1-E8 have been swapped with electrodes E9-E16, values corresponding to these groups of electrodes in the replacement connected electrode profile can be swapped and the agreement values can be recalculated based on the swapped values. If the recalculated agreement values satisfy the threshold, the assumed mismatch was correct. Once one or more mismatches are identified, they are presented to the user (e.g., via user interface 94) (314). In one embodiment, the presentation of the identified mismatch may include an instruction to swap the appropriate lead connectors 20. In another embodiment, the presentation of the mismatch may present the user with the option to allow the CP software to modify the stimulation parameters from the IPG 10 to match the connection of the electrodes to the IPG 10'. For example, if electrodes E1-E8 have been swapped with electrodes E9-E16, the stimulation parameters from the IPG 10 can be adjusted to redefine stimulation for E1 as stimulation for E9, and so on. In yet another embodiment, the user may be presented with the option to either reconnect the lead connectors 20 or to allow the CP software 96 to modify the stimulation parameters. If the user selects to allow the stimulation parameters to be modified to account for the mismatch (316), the parameters are updated and stimulation is enabled (310). If the user selects to physically swap the mismatched lead connectors (318), a new replacement electrode profile may be acquired from the replacement IPG 10' (304) after the electrode leads are reconnected and the process 300 may be repeated to verify that the electrodes have been connected in the same way in which they were connected to the IPG 10.

While process 300 has been described in terms of its performance on CP computer 202, it will be understood that the process 300 could also be performed on a different external device such as controller 40. In addition, the process 300 could also be modified such that it could be implemented on the replacement IPG 10'. For example, the replacement IPG 10' could receive the initial connected electrode profile either directly from the IPG 10 or from an external device that had received the connected electrode profile, collect the measurements that comprise the replacement connected electrode profile, compare the replacement profile with the initial profile to determine whether the electrodes are connected in a similar manner as they were connected to the IPG 10, and either enable stimulation or identify a mismatch in the connection of electrodes to the IPG 10'. Just as with the CP computer 202, the IPG 10' could present an indication of the mismatch (e.g., via communication to an external device) or update the stimulation parameters received from the IPG 10 in accordance with the identified mismatch.

Figure 14:
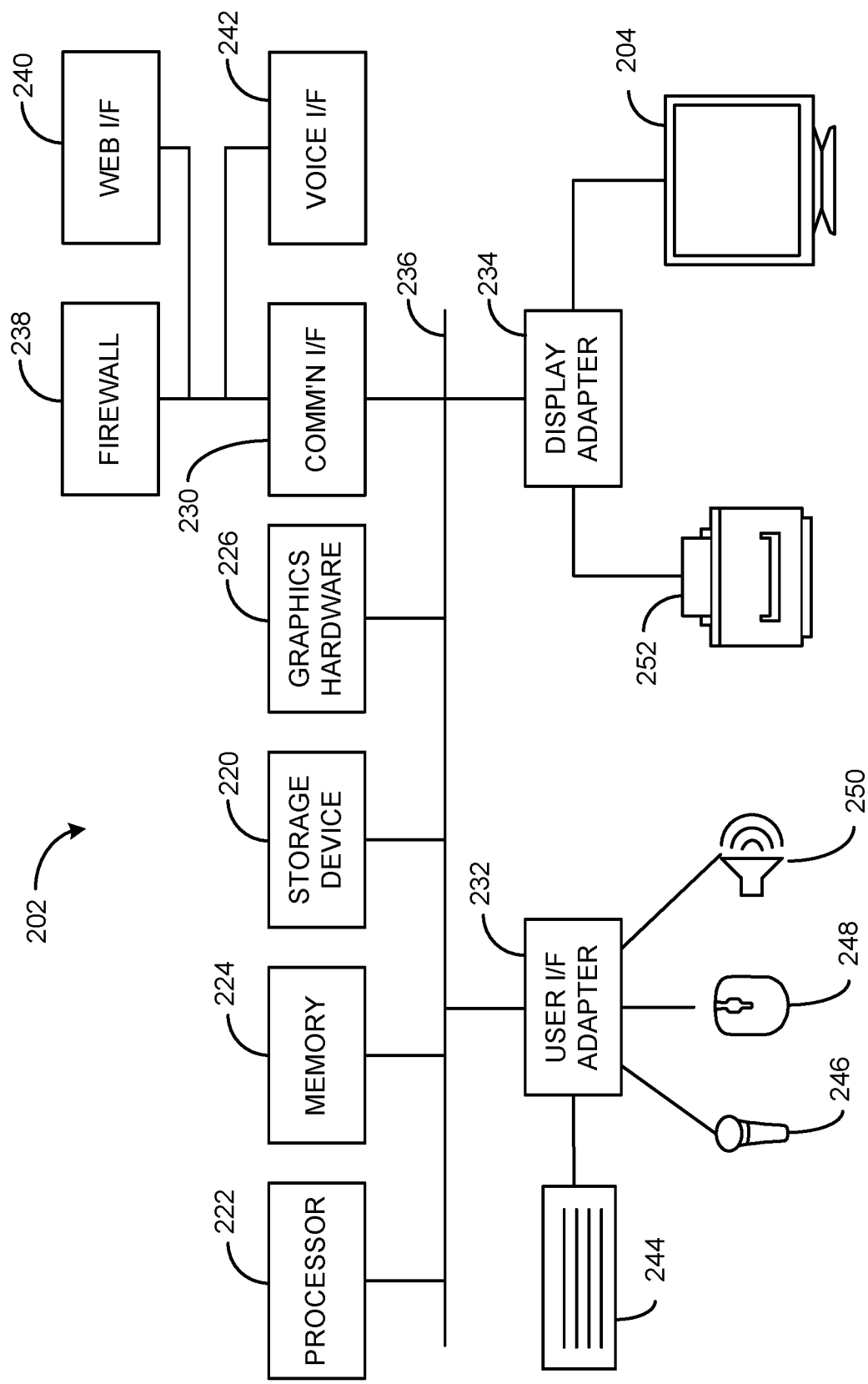
FIG. 14 shows a representative computing environment on which software that provides a process for evaluating the connection of electrodes in a replacement IPG may be executed in accordance with an aspect of the disclosure.

FIG. 14 illustrates the various components of an example CP computer 202 that may be configured to execute CP software 96 that incorporates the process 300. The CP computer 202 can include the processor 222, memory 224, storage 220, graphics hardware 226, communication interface 230, user interface adapter 232 and display adapter 234—all of which may be coupled via system bus or backplane 236. Memory 224 may include one or more different types of media (typically solid-state) used by the processor 222 and graphics hardware 226. For example, memory 224 may include memory cache, read-only memory (ROM), and/or random access memory (RAM). Storage 220 may store media, computer program instructions or software (e.g., CP software 96), preference information, device profile information, and any other suitable data. Storage 220 may include one or more non-transitory computer-readable storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), Electrically Erasable Programmable Read-Only Memory (EEPROM), and USB or thumb drive. Memory 224 and storage 220 may be used to tangibly retain computer program instructions or code organized into one or more modules and written in any desired computer programming language. Communication interface 230 (which may comprise, for example, the ports 206 or 208) may be used to connect the CP computer 202 to a network. Communications directed to the CP computer 202 may be passed through a protective firewall 238. Such communications may be interpreted via web interface 240 or voice communications interface 242. Illustrative networks include, but are not limited to: a local network such as a USB network; a business' local area network; or a wide area network such as the Internet. User interface adapter 232 may be used to connect a keyboard 244, microphone 246, pointer device 248, speaker 250 and other user interface devices such as a touch-pad and/or a touch screen (not shown). Display adapter 234 may be used to connect display 204 and printer 252.

Processor 222 may include any programmable control device. Processor 222 may also be implemented as a custom designed circuit that may be embodied in hardware devices such as application specific integrated circuits (ASICs) and field programmable gate arrays (FPGAs). The CP computer 202 may have resident thereon any desired operating system.

While the CP system 200 has been described and illustrated as communicating directly with the IPG 10, the CP system 200 may additionally or alternatively be configured to communicate with different types of neurostimulators. For example, the CP system 200 may interface with an external trial stimulator that mimics the operation of the IPG 10 but that is positioned outside of the body to evaluate therapies during a trial phase. As will be understood, the CP software 96 may be stored on a medium such as a CD or a USB drive, pre-loaded on a computing device such as the CP computer 202, or made available for download from a program repository via a network connection. Moreover, while process 300 has been described as being performed on an external device, certain portions of the process 300 may instead be performed by the IPG 10' itself. In that regard, the IPG 10' may similar components to those described with respect to CP computer 202, although various components will obviously be omitted or adapted for use in an implantable device.

Although particular embodiments have been shown and described, it should be understood that the above discussion is not intended to limit the present disclosure to these embodiments. It will be obvious to those skilled in the art that various changes and modifications may be made without departing from the spirit and scope of the present disclosure. Thus, the present disclosure is intended to cover alternatives, modifications, and equivalents that may fall within the spirit and scope of the claims.

What is claimed is:

1. A replacement implantable medical device, comprising control circuitry that is configured to:

measure one or more first electrical parameters associated with one or more of a plurality of electrodes that are connected to the replacement implantable medical device;

generate a replacement profile from the measured one or more first electrical parameters;

receive a prior profile that was generated from measurements of one or more second electrical parameters associated with the one or more of the plurality of electrodes when they were connected to a prior implantable medical device; and compare the replacement profile with the prior profile to determine whether the plurality of electrodes are connected to the replacement implantable medical device in a same manner as they were connected to the prior implanted medical device.

2. The replacement implantable medical device of claim 1, wherein the control circuitry is configured to enable the replacement implantable medical device to provide stimulation when it is determined that the plurality of electrodes are connected to the replacement implantable medical device in the same manner as the plurality of electrodes were connected to the prior implanted medical device.

3. The replacement implantable medical device of claim 2, wherein the control circuitry is further configured to receive stimulation parameters used by the prior implanted medical device and to provide stimulation using the received stimulation parameters.

4. The replacement implantable medical device of claim 1, wherein the control circuitry is further configured to identify a mismatch between the connection of the plurality of electrodes to the replacement implantable medical device and the connection of the plurality of electrodes to the prior implanted medical device.

5. The replacement implantable medical device of claim 4, wherein the control circuitry is further configured to receive stimulation parameters used by the prior implanted medical device and to adjust the stimulation parameters based on the identified mismatch.

6. The replacement implantable medical device of claim 1, wherein the one or more first and second electrical parameters comprise a measure of impedance between one or more pairs of the plurality of electrodes, or wherein the one or more first and second electrical parameters comprise a measure of impedance between one or more of the plurality of electrodes and a case electrode.

7. The replacement implantable medical device of claim 1, wherein the one or more first and second electrical parameters comprise an electric potential that is induced at one or more of the plurality of electrodes when a current is passed through one or more of the plurality of electrodes.

8. The replacement implantable medical device of claim 1, wherein the plurality of electrodes are positioned on a plurality of electrode leads that are implanted in a patient, wherein each of the plurality of electrode leads comprises one or more lead connectors that are each inserted into a port in the replacement implantable medical device.

9. A method involving a replacement implantable medical device that replaces a prior implantable medical device, the method comprising:

measuring one or more first electrical parameters associated with one or more of a plurality of electrodes that are connected to the replacement implantable medical device;

generating a replacement profile from the measured one or more first electrical parameters;

receiving a prior profile that was generated from measurements of one or more second electrical parameters associated with the one or more of the plurality of electrodes when they were connected to a prior implantable medical device; and comparing the replacement profile with the prior profile to determine whether the plurality of electrodes are connected to the replacement implantable medical device in a same manner as they were connected to the prior implanted medical device.

10. The method of claim 9, further comprising enabling the replacement implantable medical device to provide stimulation when it is determined that the plurality of electrodes are connected to the replacement implantable medical device in the same manner as the plurality of electrodes were connected to the prior implanted medical device.

11. The method of claim 10, further comprising receiving stimulation parameters used by the prior implanted medical device, and providing stimulation at the replacement implantable medical device using the received stimulation parameters.

12. The method of claim 9, further comprising identifying a mismatch between the connection of the plurality of electrodes to the replacement implantable medical device and the connection of the plurality of electrodes to the prior implanted medical device.

13. The method of claim 12, further comprising receiving stimulation parameters used by the prior implanted medical device and adjusting the stimulation parameters at the replacement implantable medical device based on the identified mismatch.

14. The method of claim 9, wherein the one or more first and second electrical parameters comprise a measure of impedance between one or more pairs of the plurality of electrodes, or wherein the one or more first and second electrical parameters comprise a measure of impedance between one or more of the plurality of electrodes and a case electrode.

15. The method of claim 9, wherein the one or more first and second electrical parameters comprise an electric potential that is induced at one or more of the plurality of electrodes when a current is passed through one or more of the plurality of electrodes.

16. The method of claim 9, wherein the plurality of electrodes are positioned on a plurality of electrode leads that are implanted in a patient, wherein each of the plurality of electrode leads comprises one or more lead connectors that are each inserted into a port in the replacement implantable medical device.

* * * * *